(12) United States Patent
Girard

(10) Patent No.: US 7,363,830 B2
(45) Date of Patent: Apr. 29, 2008

(54) DISCRETE VOLUME SAMPLING DEVICE USING A VACUUM

(75) Inventor: Lee J. Girard, Cedar Rapids, IA (US)

(73) Assignee: Vector Corporation, Marion, IA (US)

( * ) Notice: Subject to any disclaimer, the term of this patent is extended or adjusted under 35 U.S.C. 154(b) by 177 days.

(21) Appl. No.: 11/380,288

(22) Filed: Apr. 26, 2006

(65) Prior Publication Data

US 2007/0251335 A1 Nov. 1, 2007

(51) Int. Cl.
  *G01N 1/20* (2006.01)
  *G01N 1/14* (2006.01)
(52) U.S. Cl. .............. 73/863.42; 73/863.71; 73/863.81; 73/864.35; 73/864.51
(58) Field of Classification Search ........... 73/863.41, 73/863.42, 863.51, 863.52, 863.71, 863.81, 73/864.31, 864.33, 864.34, 864.35, 864.51, 73/864.52
See application file for complete search history.

(56) References Cited

U.S. PATENT DOCUMENTS

| | | | | |
|---|---|---|---|---|
| 3,263,909 A * | 8/1966 | Mazepa | ............... | 415/199.3 |
| 3,575,055 A * | 4/1971 | Thornton, Jr. | ........... | 73/863.43 |
| 3,588,944 A * | 6/1971 | Fromknecht et al. | ...... | 15/327.2 |
| 3,735,641 A * | 5/1973 | Bink et al. | ............... | 73/863.43 |
| 3,750,478 A * | 8/1973 | Keene | ............... | 73/863.44 |
| 3,782,200 A * | 1/1974 | Maas | ............... | 73/863.51 |
| 4,026,154 A * | 5/1977 | Pfeiffer et al. | ........... | 73/863.44 |
| 4,037,476 A | 7/1977 | McCrabb | | |
| 4,283,946 A | 8/1981 | Bowser et al. | | |
| 4,286,466 A * | 9/1981 | Stewart | ............... | 73/863.83 |
| 4,395,164 A | 7/1983 | Beltrop et al. | | |
| 4,418,581 A * | 12/1983 | Jones | ............... | 73/864.34 |
| 4,466,761 A | 8/1984 | Beltrop et al. | | |
| 4,574,645 A * | 3/1986 | Allen et al. | ............... | 73/863.51 |
| 4,712,434 A * | 12/1987 | Herwig et al. | ........... | 73/864.63 |
| 4,854,180 A * | 8/1989 | Mauleon et al. | ......... | 73/863.86 |
| 4,930,359 A * | 6/1990 | Wolfrum et al. | ......... | 73/863.23 |
| 5,211,062 A * | 5/1993 | Moser | ............... | 73/864.33 |
| 5,265,483 A * | 11/1993 | Farrell et al. | ............ | 73/863.86 |
| 5,309,773 A * | 5/1994 | Tokoyama | ............... | 73/863.01 |
| 5,408,890 A * | 4/1995 | Klaus | ............... | 73/863.81 |
| 5,433,120 A * | 7/1995 | Boyd et al. | ............... | 73/863.81 |
| 5,437,201 A * | 8/1995 | Krueger | ............... | 73/864.35 |
| 5,437,202 A * | 8/1995 | Clark, II | ............... | 73/864.35 |
| 6,453,759 B1 * | 9/2002 | Lebski et al. | ............ | 73/864.34 |
| 6,546,819 B1 * | 4/2003 | Schadt et al. | ............ | 73/863.71 |
| 6,780,818 B2 | 8/2004 | Gundel et al. | | |
| 6,843,103 B2 * | 1/2005 | Aguilera et al. | ........... | 73/28.01 |
| 7,168,332 B2 * | 1/2007 | Orange et al. | ........... | 73/863.44 |
| 7,253,005 B2 * | 8/2007 | Coute et al. | ................ | 436/174 |
| 2002/0162509 A1* | 11/2002 | Hakes | ............... | 119/14.02 |

* cited by examiner

*Primary Examiner*—Hezron Williams
*Assistant Examiner*—David A. Rogers
(74) *Attorney, Agent, or Firm*—McKee, Voorhees & Sease, P.L.C.

(57) ABSTRACT

A discrete volume vacuum sampling device is provided with a vacuum tube, a sample tube, and a sample container. The container defines a discrete volume of product to be sampled from a product bed within a processing machine. The sampler tube extends between the container and the machine containing the product to be sampled. When a vacuum is applied through the vacuum tube, a door on the container is pulled shut, thereby increasing air velocity in the sampler tube, so as to draw product from the bed upwardly through the sampler tube and into the container. When the container is full, the vacuum is stopped, such that the weight of the product in the container pushes the door open for discharge of the discrete volume of product sample, while product remaining within the sampler tube is discharged back into the bed of material within the machine.

15 Claims, 4 Drawing Sheets

US 7,363,830 B2

DISCRETE VOLUME SAMPLING DEVICE USING A VACUUM

BACKGROUND OF THE INVENTION

Particulate materials are often processed either in batch or continuous operations. For example, rotating drums can be used to dry particulate material and/or coat particular material with a sprayed solution. The materials being processed are of various types. For example, pharmaceutical tablets are coated in rotating drums, in both batch and continuous operations. Agricultural seeds are also coated with pesticides, herbicides, and fungicides in rotating drums. Cereals and snack foods are also processed in rotating drums to add flavor, which is sprayed onto the particles and then dried. These processes may require sampling of the product for quality assurance. Various prior art sampling techniques exist. For example, an operator can reach into the machine with a scoop to retrieve product. However, such a manual sampling process may be prohibited by process parameters, such as temperature and airflow conditions which require that the door of the machine stay sealed. Also, manual sampling of the product may create contamination concerns, which must be avoided. Manual sampling also creates safety issues, particularly due to dangers of the machine mechanics or biological hazards of certain products or coating solutions.

Various automatic sampling systems have been developed to overcome the problems with manual sampling. Vacuum transport is known for moving or transferring products, but has one major drawback when used for product sampling. Generally, a basic vacuum transfer system is good at moving all of the product from a specified area to another location, however, does not provide a discrete sample volume. Limiting the vacuum to a specific time period limits the volume of product that is suctioned, but still allows for various sample volumes, due to the difficultly in controlling the amount of product that is vacuumed up by the system. Such a vacuum system is not satisfactory where precision and repeatability are critical for validation, such as in the pharmaceutical industry.

Therefore, a primary objective of the present invention is the provision of an improved discrete volume vacuum sampling system for particulate materials.

Another objective of the present invention is the provision of an improved device for sampling a discrete volume of particulate material from a bed of material.

A further objective of the present invention is the provision of an improved method of obtaining a discrete volume sample of particulate material from a bed of material.

Another objective of the present invention is the provision of a product sampling device using a vacuum to obtain a discrete volume of product for sampling.

Still another objective of the present invention is the provision of a vacuum system for product sampling wherein a container door is automatically closed when the vacuum is applied and automatically opened when the vacuum is released.

Another objective of the present invention is the provision of a product vacuum sampling system which discharges excess product back into the product bed.

Another objective of the present invention is the provision of is a discrete volume vacuum sampling system which is simple and accurate.

These and other objectives will become apparent from the following description of the invention.

BRIEF SUMMARY OF THE INVENTION

The discrete volume vacuum sampling device of the present invention is used to obtain precise and repeatable product volume samples from a bed of particulate material. The device includes an inclined sample tube with the lower end extending into the product bed, and an upper end connected to a sample container. A vacuum tube is connected to the sample container and to a vacuum source. The container includes a pivotal door on the lower end which is automatically moved to a closed position by the negative pressure in the container when the vacuum is applied, and automatically moved to the open position by the weight of product in the container when the vacuum is released. Upon actuation of the vacuum source, particles from the bed are drawn through the sample tube and deposited in the container. Upon deactuation of the vacuum source, particles in the container are discharged through the door, while particles in the sample tube are discharged back into the bed. A screen at the upper end of the container or the lower end of the vacuum tube prevents products from being drawn into the vacuum tube.

DETAILED DESCRIPTION OF THE PREFERRED EMBODIMENT

Figure 1:
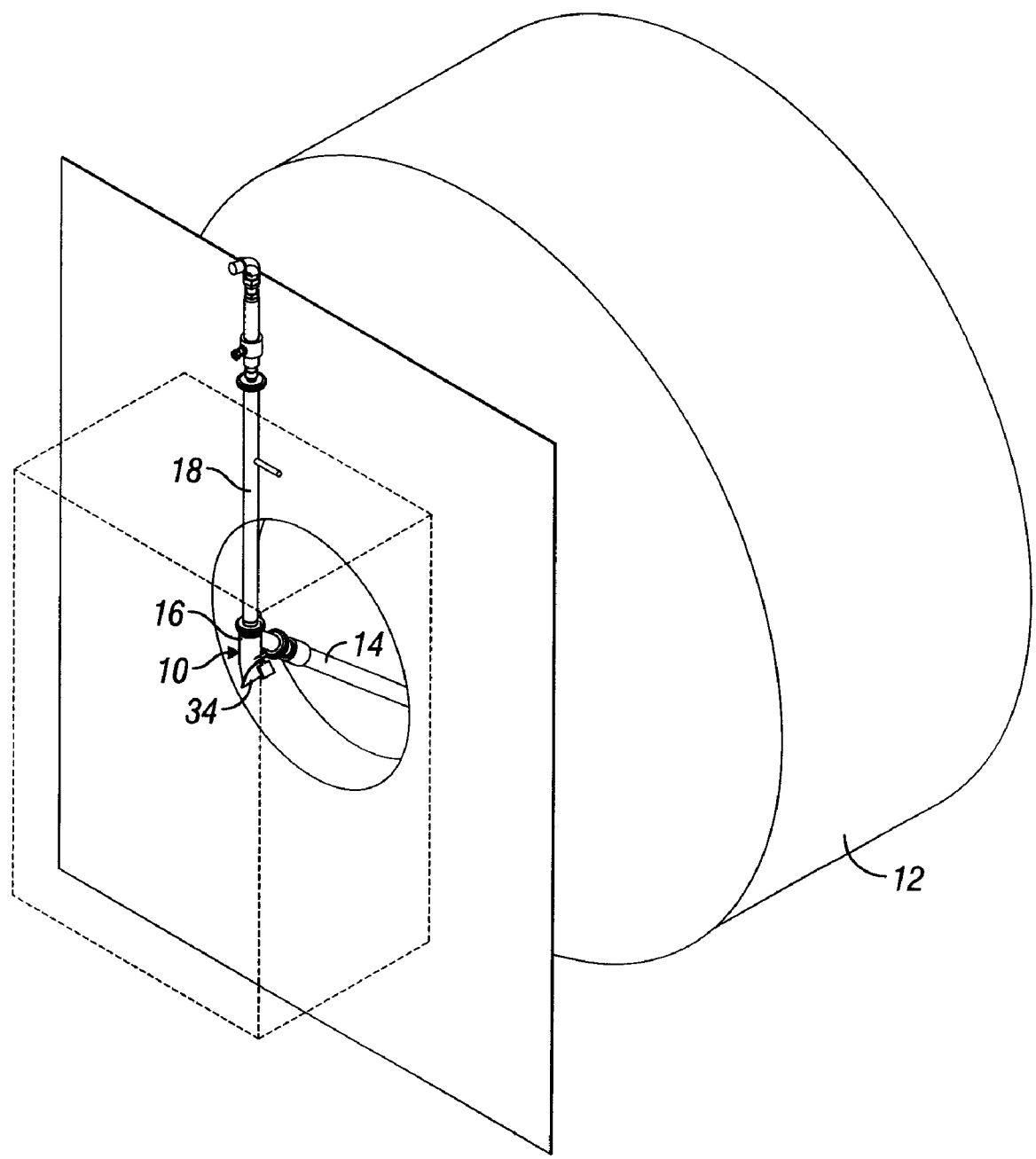
FIG. 1 is a perspective view of a preferred embodiment of the discrete volume vacuum sampling device of the present invention.
Figure 2:
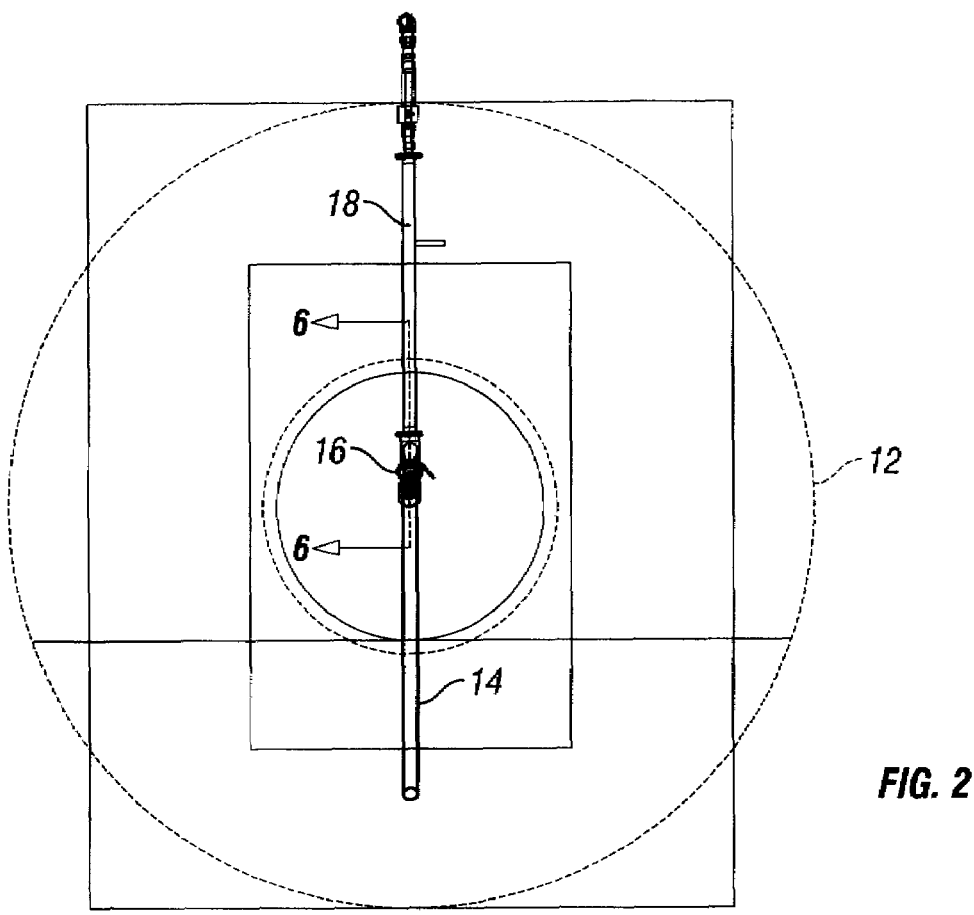
FIG. 2 is a front elevation view of the device shown in FIG. 1.
Figure 3:
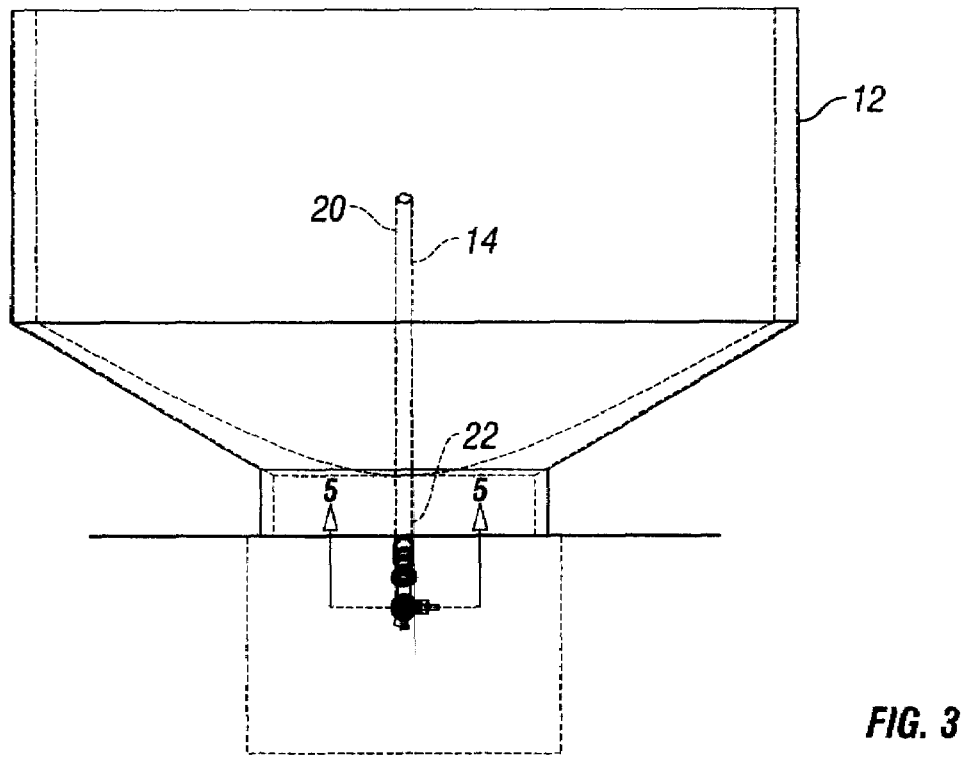
FIG. 3 is a top elevation view of the device shown in FIG. 1.
Figure 4:
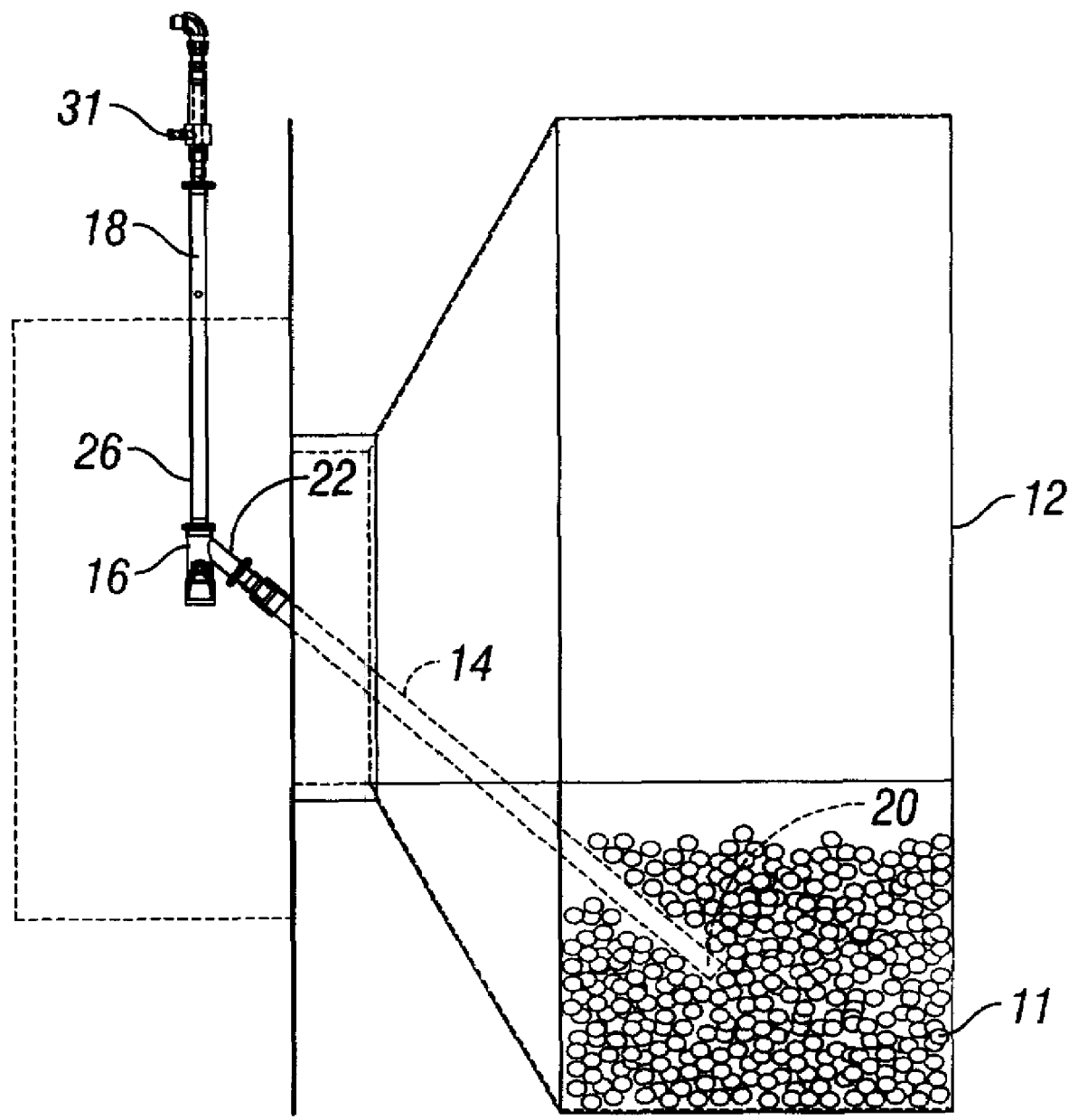
FIG. 4 is a side elevation of the device.
Figure 5:
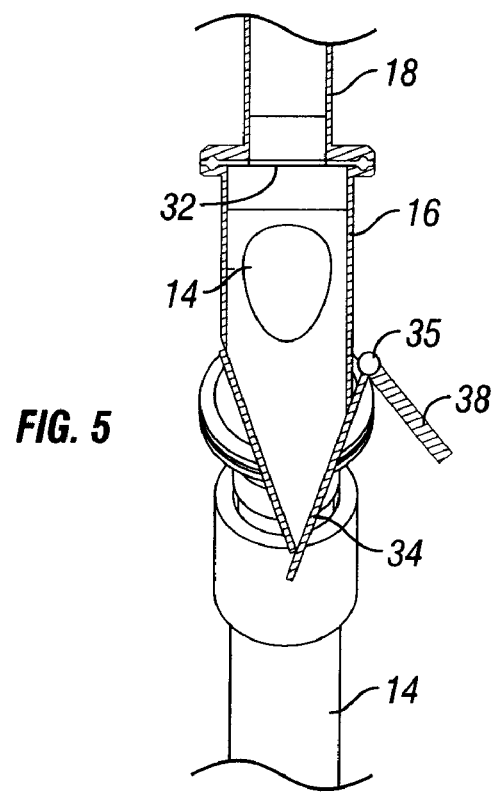
FIG. 5 is sectional view taken along lines 5-5 of FIG. 3, with the door in a closed position.
Figure 6:
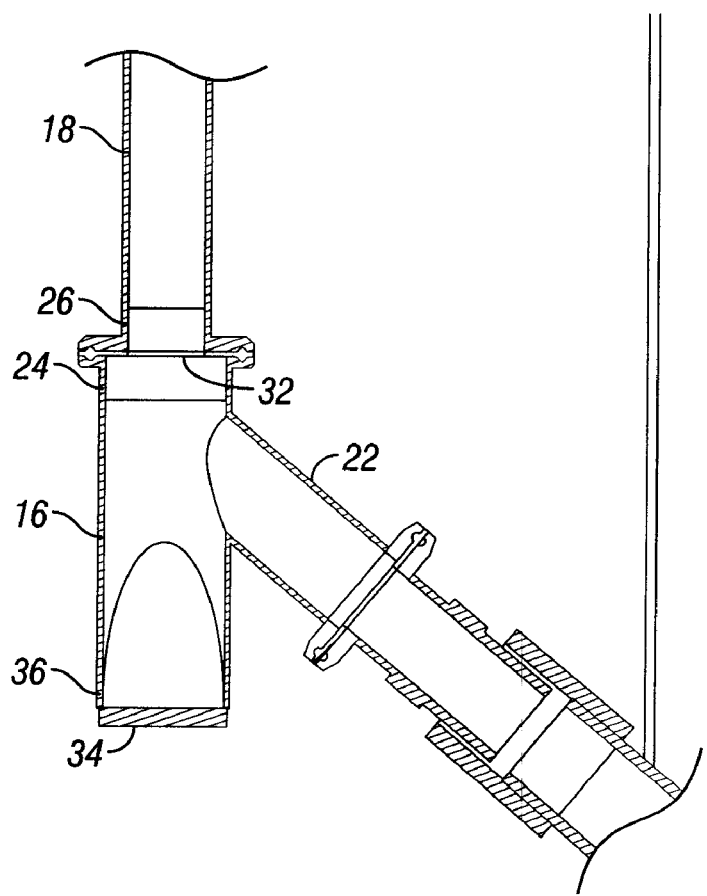
FIG. 6 is a sectional view taken along lines 6-6 of FIG. 2.

The device of the present invention is designated by the numeral 10 in the drawings. The device 10 can be used to withdraw product samples from any type of a vessel, drum or machine 12 which holds a bed 11 of particulate material products for processing. The machine 12 may be a batch system or a continuous system for processing the particles. For example, the machine 12 may be a rotatable drum having one or more nozzles for spraying a coating solution onto the particulate material within the drum as the drum rotates. The drum 12 may be perforated to facilitate drying of the coating solution on the particles. The particles may be any of a wide variety of products which are typically processed in the machine 12, such as pharmaceutical tablets, agricultural seeds, cereal, and snack foods. The machine 12 may also be used for drying product, with or without a spray coating solution.

The device 10 includes a sample tube 14, a sample container 16, and a vacuum tube 18. The sample tube 14 is inclined, and includes a lower end 20 adapted to reside within the product bed 11 within the machine 12, and an upper end 22 connected adjacent the upper end 24 of the container 16. The vacuum tube 18 has a lower end 26 connected to the upper end 24 of the container 16, and an upper end 28. In one embodiment, the upper end 28 of the vacuum tube 18 is connected to an educator 30 having a port 31 through which compressed air is supplied so as to create a negative pressure in the vacuum tube 18. In another embodiment, the upper end 28 of the vacuum tube 18 may be connected to a vacuum pump (not shown) to create a vacuum in the tube 18. A screen 32 is provided in the upper end 24 of the container 16 or the lower end 26 of the vacuum tube 18, or at the juncture of the container 16 and tube 18.

A door 34 is pivotally mounted about a hinge on axis 35 on the lower end 36 of the container 16. The door 34 is adapted to move between open and closed positions over the open lower end 36 of the container 16. The door 34 is normally free to open when the device 10 is not in use, with a small gap residing between the door 34 and the lower end 36 of the container 16.

In use, the lower end 20 of the sampler tube 14 is positioned within the machine 12 so as to be embedded within the bed 11 of particulate material being processed in the machine 12. The vacuum source 30 is actuated, thereby creating a negative pressure within the container 16 and the vacuum tube 18. The negative pressure pulls the door 34 closed into a sealing engagement with the lower end 36 of the container 16. The applied vacuum draws particulate material from the bed 11 upwardly through the sample tube 14, which deposits the withdrawn product into the container 16. The screen 32 prevents product from being sucked into the vacuum tube 18. Application of the vacuum continues until the container 16 is filled with the product sample withdrawn from the bed 11. When the container 16 is full, the product stops transferring through the sample tube 14. The vacuum source 30 is then deactivated to discontinue the vacuum, and thereby remove the negative pressure within the tube 18. The weight of the product within the container 16 pushes the door 34 open such that the product is discharged from the open lower end 36 of the container 16 into a receptacle (not shown). Also, product within the sample tube 14 which could not enter the full container 16 falls back through the sample tube 14 into the product bed 11 within the machine 12.

When the vacuum source 30 is activated, air is drawn out of the device 10 at the upstream end of the vacuum tube 18, which, in turn, draws air into the device 10 through the open lower end 36 of the container 16 and through the sample tube 14. Initially, the air velocity in the sample tube 14 may be insufficient to pull product from the bed 11 into the tube 12. However, when the air velocity through the opened end 36 of the container 16 is sufficient, the door 34 will be pulled closed, and air velocity in the sample tube 14 will increase to the point that product is drawn from the bed 11 in the machine 12 into the container 16. Preferably, the door 34 is in sealing engagement with the lower end 36 of the container when in the closed position.

The container door 34 is balanced with a counter-weight 38 such that a minimal gap normally exists between the lower end 36 of the container 16 and the door 34, but also allows the weight of the product within the container 16 to push the door 34 open in the absence of a vacuum. The gap between the lower end 36 of the container 16 and the door 34 is sufficiently small to allow the air flow generated by the vacuum source 30 to pull the door 34 to the closed position. The force generated by the negative pressure within the container 16 is sufficient to overcome the weight of the product in the container 16 when the vacuum is applied. When the door 34 closes, the air velocity that develops within the sample tube 14 is sufficient to draw product from the bed 11 in the machine 12 upwardly through the tube 14 and into the container 16.

In normal operation of the machine 12, the sample tube 14 is preferably out of the product bed. When a sample needs to be taken, the lower end 20 of the sample tube 14 is extended into the product bed within the machine 12.

The container 16 thus provides a discrete sample volume, which can be deposited into any conventional receptacle. The sampling device 10 can be used while the machine 12 is processing the particulate material product within the machine.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A device for sampling a discrete volume of particulate material from a bed of material, comprising:
   a sample tube having upper and lower ends, with the lower end being adapted to be positioned in the bed;
   a sample container connected to the upper end of the sample tube;
   a vacuum tube connected to the sample container;
   a door pivotally mounted on the container to automatically move between open and closed positions;
   a vacuum source connected to the vacuum tube;
   whereby upon actuation of the vacuum source, particles from the bed are drawn through the sample tube and deposited in the container; and
   whereby upon deactuation of the vacuum source, particles in the container will discharge through the door and particles in the sample tube will discharge back into the bed.

2. The device of claim 1 further comprising a screen adjacent the juncture of the container and the vacuum tube to preclude material from being drawn up the vacuum tube.

3. The device of claim 1 wherein the sample tube is inclined.

4. The device of claim 1 wherein the door moves to a closed position in response to application of a vacuum to the container.

5. The device of claim 1 wherein the door is open in the absence of a vacuum.

6. The device of claim 1 wherein the vacuum source is upstream from the container and the sample tube.

7. A product sampling device, comprising:
   a container defining a discrete volume of product to be sampled;
   a sampling tube extending between the container and a vessel containing the product to the sampled;
   a vacuum tube to apply a vacuum to the sampling tube so as to draw product from the vessel, through the sampling tube and into the container;
   a door on the container automatically moveable to a closed position when the vacuum is applied so as to retain product in the container and automatically moveable to an open position when the vacuum is released so as to discharge the discrete volume of product from the container.

8. The product sampling of claim 7 wherein the sampling tube angles downwardly from the container so that product in the sampling tube discharges into the vessel when the vacuum is released.

9. The product sampling of claim 7 further comprising a screen to preclude particles from passing into the vacuum tube.

10. The product sampling of claim 7 further comprising a vacuum source connected to the vacuum tube.

11. The product sampling of claim 7 wherein the sampling tube has an upper end connected adjacent an upper end of the container.

12. A method of obtaining a discrete volume sample of particulate material from a bed of particulate material, comprising:
  applying a vacuum through a vacuum tube to a sample tube extending into the bed to draw material up the tube;
  depositing the material in the sample tube into a container until the container is full;
  discontinuing the vacuum;
  discharging the material in the container;
  discharging material in the sample tube back into the bed; and
  automatically closing a door on the container when the vacuum is applied and automatically opening the door when the vacuum is discontinued.

13. The method of claim 12 further comprising blocking the material in the sample tube from entering the vacuum tube.

14. The method of claim 12 wherein the material is discharged from the container by gravity.

15. The method of claim 12 wherein the material is discharged from the sample tube by gravity.

* * * * *